(12) United States Patent
Brune et al.

(10) Patent No.: US 10,371,605 B2
(45) Date of Patent: Aug. 6, 2019

(54) PNEUMATIC MINE DUST SAMPLING INSTRUMENT

(71) Applicant: Colorado School of Mines, Golden, CO (US)

(72) Inventors: Jurgen Brune, Morrison, CO (US); Ben Goertz, Golden, CO (US); Gregory Bogin, Superior, CO (US); Sean McDaniel, Riverton, WY (US); Tyler Rockley, Golden, CO (US); Flavia Soares Barreto, Minas Gerais (BR); Vinay Duddempudi, Alexandria, VA (US); Katherine Ann Robert, Englewood, CO (US); Nick Kapela, Longmont, CO (US)

( * ) Notice: Subject to any disclaimer, the term of this patent is extended or adjusted under 35 U.S.C. 154(b) by 234 days.

(21) Appl. No.: 15/332,267

(22) Filed: Oct. 24, 2016

(65) Prior Publication Data

US 2017/0115188 A1 Apr. 27, 2017

Related U.S. Application Data

(60) Provisional application No. 62/245,156, filed on Oct. 22, 2015.

(51) Int. Cl.
| | |
|---|---|
| *G01N 1/04* | (2006.01) |
| *G01N 1/22* | (2006.01) |
| *E21F 5/08* | (2006.01) |
| *G01N 1/02* | (2006.01) |
| *G01N 1/10* | (2006.01) |
| *G01N 33/24* | (2006.01) |

(52) U.S. Cl.
CPC ............... *G01N 1/04* (2013.01); *E21F 5/08* (2013.01); *G01N 1/2273* (2013.01); *G01N 33/24* (2013.01); *G01N 2001/028* (2013.01); *G01N 2001/1006* (2013.01)

(58) Field of Classification Search
CPC ....... G01N 2001/028; G01N 2001/022; G01N 1/24; G01N 1/22; G01N 1/2214; G01N 1/02; G01N 2001/2223; G01N 1/2273; G01N 1/2294; G01N 2001/2276; G01N 33/227; G01N 33/48714
See application file for complete search history.

(56) References Cited

U.S. PATENT DOCUMENTS

| | | | | |
|---|---|---|---|---|
| 2009/0250382 | A1* | 10/2009 | Moore | ............ B08B 5/02 209/133 |
| 2015/0153255 | A1* | 6/2015 | Asami | ............ G01N 1/2252 73/23.31 |

OTHER PUBLICATIONS

"Coal Mine Safety and Health General Inspection Procedures Handbook," Mine Safety and Health Administration, Handbook No. PH13-V-I, Feb. 2013, 276 pages, submitted in two parts.

(Continued)

*Primary Examiner* — Peter J Macchiarolo
*Assistant Examiner* — Anthony W Megna Fuentes
(74) *Attorney, Agent, or Firm* — Sheridan Ross PC

(57) ABSTRACT

Mine dust in underground coal mines is potentially explosive and must be sampled and tested for sufficient inert content regularly. The present invention comprises a pneumatic mine dust sampling instrument equipped with a specially designed nozzle arrangement that delivers a controlled pulse of air which entrains the mine dust, similar to the entrainment process that happens during a mine explosion. The entrained mine dust can then be collected and tested for compliance with applicable federal standards.

19 Claims, 7 Drawing Sheets

(56) References Cited

OTHER PUBLICATIONS

Cokljat et al., "Multiphase k-epsilon models for unstructured meshes," Proceedings of ASME FEDSM 2000: ASME 2000 Fluids Engineering Division Summer Meeting, Boston, MA, 2000, 6 pages.
Nagy et al., "Float Coal Hazard in Mines: A Progress Report," U.S. Bureau of Mines, RI No. 6581, 1965.
Sapko et al., "Explosibility of float coal dust distributed over a coal-rock dust substratum," Proc. 22nd International Conference of Safety in Mines Research Institutes, 1987, pp. 459-468.

\* cited by examiner

PNEUMATIC MINE DUST SAMPLING INSTRUMENT

CROSS-REFERENCE TO RELATED APPLICATIONS

This application claims priority and benefit under 35 U.S.C. § 119(e) to U.S. Provisional Patent Application Ser. No. 62/245,156, filed on Oct. 22, 2015, entitled "Pneumatic Mine Dust Sampling Instrument," which is hereby incorporated by reference.

FIELD OF THE INVENTION

The present invention relates to the field of mine dust sampling and, more specifically, to devices and methods for collecting mine dust samples.

BACKGROUND OF THE INVENTION

The 2010 disaster at the Upper Big Branch mine in West Virginia demonstrated the destructive violence of a coal dust explosion by killing 29 miners in the worst mining accident the United States had experienced in almost 40 years. A major contributing factor to this explosion was that mine operators did not then have a reliable and repeatable way of objectively sampling mine dust before it is analyzed for its combustible/explosive and inert composition.

Coal dust in underground coal mines is potentially explosive. Stone dust is added to the coal dust to render the combined mine dust inert. To demonstrate and document inertization, mine dust must be sampled regularly. Samples are analyzed on-site and in the laboratory to confirm that they comprise at least 80% inert components, as required by 30 C.F.R. § 75.403, to prevent devastating coal dust explosions. Currently, mine dust samples are taken with a pan and brush to an estimated depth of ⅛ inch, following sampling guidelines by the U.S. Mine Safety and Health Administration (MSHA). This method of sampling is subjective and does not take into account that an explosion scours up mine dust through pneumatic entrainment. Therefore, samples collected mechanically with a pan and brush may not correctly reflect the portion of mine dust that would be scoured up during an explosion. Additionally, samples collected using the pan-and-brush method are subject to human error (resulting, for example, from failure to collect all brushed dust in the pan, and/or failure to brush to a depth of ⅛ inch) and inconsistent results (due, for example, to the difficulty of applying the same brushing force during every sample collection, and to the difficulty of brushing to a depth of exactly ⅛ inch). Still further, the pan-and-brush method of collecting dust samples is time consuming, requiring careful brushing of a dusty surface to ensure that the proper amount of dust is collected. Suitable instruments for, and an accurate, consistent method of, collecting rock dust samples to test for explosibility do not currently exist.

SUMMARY

Fundamentally, mine dust particles must be entrained in air to participate in and propagate a coal dust explosion. Any form of mechanical sample collection, for example with scoops or brushes, is thus unsatisfactory because it does not accurately mimic the dust entrainment process that happens in an explosion. Current MSHA guidelines require sampling mine dust with a brush and dust pan, removing the "uppermost ⅛th inch (approximate depth)." The prescribed brush action is questionable since the bristles can dislodge dust particles with much greater force compared to entrainment in air flow. Yet, only those dust particles that may be entrained in air will participate in an explosion. A coal dust explosion typically scours up the top 0.7 to 2.6 mm (0.02 to 0.1 inch) of dust. Sapko et al., have shown that a paper-thin layer (~0.12 mm) of coal dust is already sufficient for propagation of a coal dust explosion. See Sapko et al., *Explosibility of float coal dust distributed over a coal-rock dust substratum*, Proc. 22nd International Conference of Safety in Mines Research Institutes, 1987, pp. 459-468 (Beijing, China: China Coal Industry Publishing House). Therefore, brush sampling to an estimated depth of ⅛ inch may not constitute a relevant, objective, consistent and repeatable sampling technique.

In view of the limitations now present in the prior art techniques, the present invention provides a pneumatic dust sampling instrument equipped with a specially designed nozzle arrangement and method for using the same. The pneumatic dust sampling instrument, or dust sampling device, delivers a controlled pulse of air onto the sampling surface from which dust is to be collected. The air entrains the mine dust, similar to the entrainment process that happens during a mine explosion. The pneumatic dust sampling instrument allows mine operators to obtain repeatable, relevant, and accurate test results. The pneumatic dust sampling instrument further reduces the potential for human error to affect test results, and allows for faster testing than is possible using the traditional pan-and-brush sampling method.

Although described herein in the context of the mining field, the systems and methods of the present invention are not limited to use in the mining field, and may indeed be used in any field in which the quantity and makeup of collected dust or other particulates is pertinent. A dust sampling device as described herein may be used, for example, in clean rooms, food manufacturing facilities, and for hazardous materials testing.

Another major advantage of the pneumatic sampling method with the dust sampling device is that samples can be collected from vertical and inverted surfaces including wire mesh, belt structure, cables, water lines and the mine roof. Dust deposited in elevated areas is much more likely to be entrained in an explosion compared to floor dust.

A dust sample collecting device according to one embodiment of the present invention includes a housing, at least one nozzle, a sample collection bag, and a compressed air containment vessel. The housing comprises a front surface, a back surface, a plurality of sidewalls, and an underside. The underside has a first portion defining at least one nozzle mounting bracket and a second portion defining a collection area. The collection area has a wedge-shaped cross-section. At least one nozzle has an intake port and an exhaust port, and is attached to the nozzle mounting bracket with the exhaust port positioned at an inlet to the collection area. The exhaust port of the nozzle is configured to discharge air into the collection area at a downward angle between zero (0) and ten (10) degrees below horizontal. The sample collection bag has a single opening, which is removably attached to an outlet of the collection area to receive dust entrained by discharged air in the collection air. The compressed air containment vessel is in selective fluid communication with the intake port of the nozzle and is configured to store compressed air at a pressure between ten (10) and thirty (30) psig.

Additionally, the housing may comprise a compressed air containment vessel. The housing further comprises a plurality of resting plates, or wings, each extending horizontally from a bottom of one of the plurality of sidewalls of the housing. At least one nozzle may be configured to eject air from the exhaust port at a downward angle of approximately five (5) degrees below horizontal. The air containment vessel may store compressed air at a pressure between fifteen (15) and twenty-five (25) psig. The outlet of the collection area may be aligned with the back surface of the housing.

Further, the second portion of the underside may comprise a planar surface. The inlet of the collection area may comprise a first height, the outlet of the collection area may comprise a second height greater than the first height, a forward end of the planar surface may define an upper boundary of the inlet, and a rearward end of the planar surface may define an upper boundary of the outlet.

A method of obtaining a dust sample according to one embodiment of the present invention comprises placing a dust sampling device on a sampling surface; pressurizing a charging vessel of the dust sampling device with a charge of compressed air; discharging the charge of compressed air through a nozzle of the dust sampling device onto the sampling surface; and receiving a dust sample in a sample collection bag of the dust sampling device.

In one embodiment, the charge of compressed air may have a pressure of between 15 and 25 psig. Discharging the charge of compressed air through the nozzle may comprise discharging the charge of compressed air through the nozzle at a downward angle of between zero (0) and ten (10) degrees from horizontal. Pressurizing a charging vessel of the dust sampling device with a charge of compressed air may comprise switching a pneumatic switch of the dust sampling device from a discharge state to a charge state. The method may further comprise adjusting an adjustable regulator to a pressure between ten (10) and (30) psig, or to a pressure between fifteen (15) and twenty-five (25) psig.

In yet another embodiment of the present invention, a dust sampling device includes an air routing system, a charging vessel, and a sample chamber. The air routing system generally comprises a compressed air fitting in fluid communication with an adjustable regulator and a pneumatic trigger switch. The charging vessel is also in fluid communication with the pneumatic trigger switch. The sample chamber comprises at least one nozzle in fluid communication with a sample collection area and a sample collection bag. The at least one nozzle has an intake port in fluid communication with the pneumatic trigger switch. The pneumatic trigger switch selectively releases compressed air from the charging vessel into the intake port of the at least one nozzle, which discharges the air into the sample collection area.

Additionally, the at least one nozzle may comprise an exhaust port positioned to direct air exiting therefrom toward the sample collection area at an angle between zero (0) and ten (10) degrees below horizontal. The sample collection area may comprise an inlet having an inlet lower boundary and an inlet upper boundary; and an outlet having an outlet lower boundary and an outlet upper boundary. The inlet lower boundary and the outlet lower boundary may define a first substantially horizontal plane, and the inlet upper boundary and the outlet upper boundary may define a second plane that intersects the first substantially horizontal plane at a point between a third plane defined by the nozzle intake port and a fourth plane defined by the nozzle exhaust port.

Further, the charging vessel may comprise an airtight container, and a pneumatic trigger switch may comprise a valve that selectively allows compressed air to flow into or out of the airtight container. A pressure setting of the adjustable regulator may determine a pressurization of a charge of compressed air in the charging vessel. The pressure setting may be between ten (10) and thirty (30) psig, or it may be between fifteen (15) and twenty-five (25) psig. The pneumatic switch may have a charging state for channeling compressed air from the compressed air fitting to the charging vessel, and a discharge state for channeling compressed air from the charging vessel to the at least one nozzle.

BRIEF DESCRIPTION OF THE DRAWINGS

The accompanying drawings, which are incorporated in and constitute a part of the specification, illustrate embodiments of the disclosure and, together with the general description of the disclosure given above and the detailed description of the drawings given below, serve to explain the principles of the disclosure.

Figure 1:
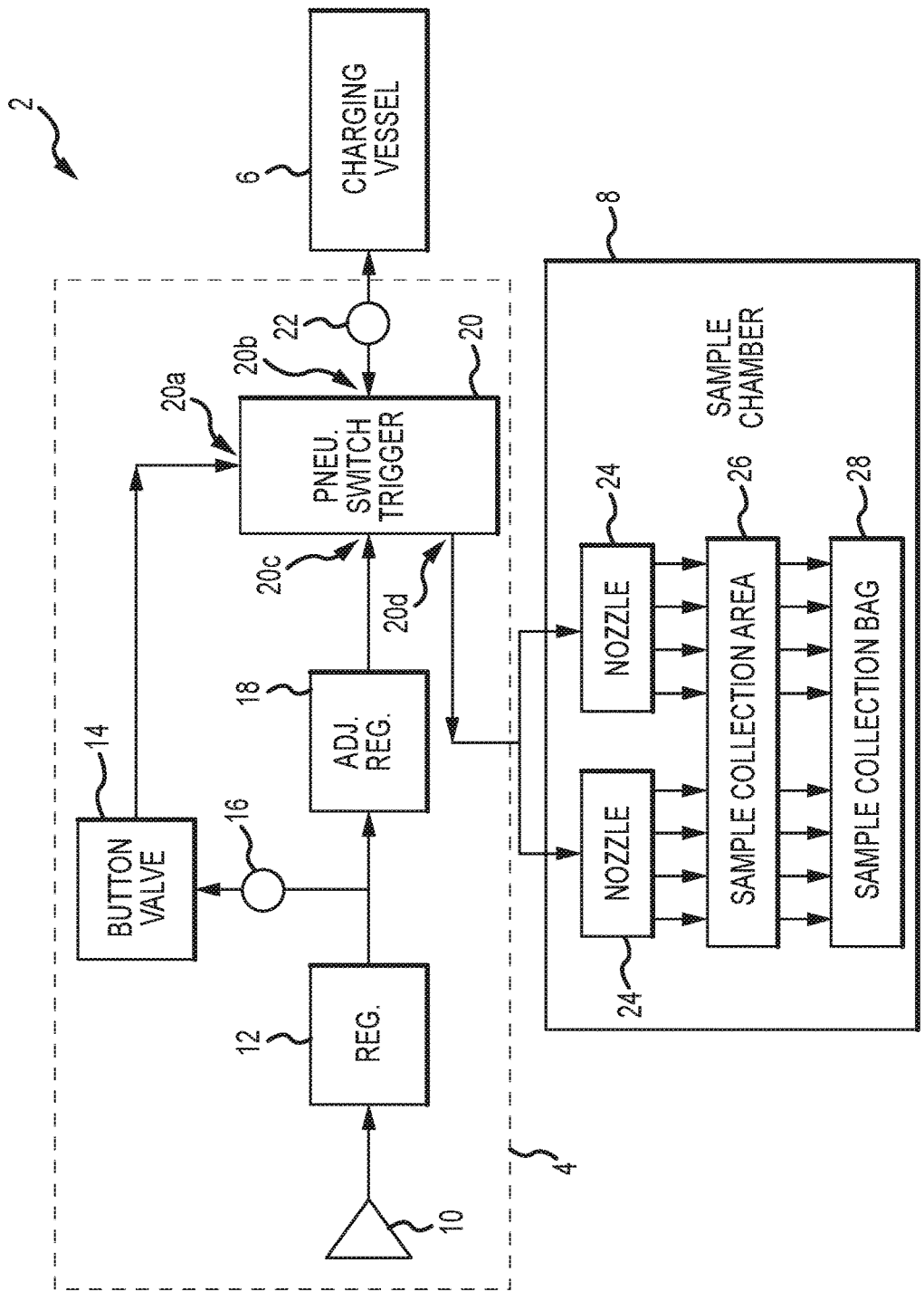
FIG. 1 depicts a block diagram of a pneumatic mine dust sampling instrument according to one embodiment of the present invention.

To assist in the understanding of the embodiments of the present invention, the following list of components and associated numbering found in the drawings is provided:

| Component No. | Component |
| --- | --- |
| 2 | Dust sampling device |
| 4 | Air routing system |
| 6 | Charging vessel |
| 8 | Sample chamber |
| 10 | Compressed air fitting |
| 12 | Regulator |
| 14 | Button valve |
| 16 | Pressure gauge |
| 18 | Adjustable regulator |
| 20 | Pneumatic switch trigger |
| 20a | Switch port |
| 20b | Switch port |
| 20c | Switch port |
| 20d | Switch port |
| 22 | Pressure gauge |
| 24 | Nozzle |
| 26 | Sample collection area |
| 28 | Sample collection bag |
| 30 | Housing |
| 32 | Mounting Bracket |
| 34 | Mounting Screw Hole |
| 36 | Resting plate |
| 38 | Sample collection area inlet |
| 40 | Sample collection area outlet |
| 42 | Gasket |
| 44 | Lid |
| 46 | Mounting screws |
| 48 | Dust bed |
| 50 | Front surface |

-continued

| Component No. | Component |
|---|---|
| 52 | Rear surface |
| 54 | Sidewall |

It should be understood that the drawings are not necessarily to scale, and various dimensions may be altered. In certain instances, details that are not necessary for an understanding of the present invention or that render other details difficult to perceive may have been omitted. It should be understood, of course, that the present invention is not necessarily limited to the particular embodiments illustrated herein.

DETAILED DESCRIPTION

The present invention has significant benefits across a broad spectrum of endeavors. It is the Applicant's intent that this specification and the claims appended hereto be accorded a breadth in keeping with the scope and spirit of the present invention being disclosed despite what might appear to be limiting language imposed by the requirements of referring to the specific examples disclosed. To acquaint persons skilled in the pertinent arts most closely related to the present invention, a preferred embodiment that illustrates the best mode now contemplated for putting the present invention into practice is described herein, by and with reference to the annexed drawings that form a part of the specification. The exemplary embodiment is described in detail without attempting to describe all of the various forms and modifications in which the present invention might be embodied. As such, the embodiments described herein are illustrative, as will become apparent to those skilled in the arts, and may be modified in numerous ways within the scope and spirit of the present invention. Indeed, numerous alternative embodiments could be implemented, using either current technology or technology developed after the filing date of this patent, which would still fall within the scope of the claims. To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning.

The current brush-and-pan sampling method required by MSHA (see *Coal Mine Safety and Health General Inspection Procedures Handbook*, Mine Safety and Health Administration, Handbook Number: PH13-V-1, February 2013 (MSHA 2013)) is flawed in several aspects: Mechanical sampling with a brush exerts forces on the mine dust that may differ significantly from those present during an explosion. Also, U.S. Bureau of Mines research (Nagy 1965) has determined that only the top 0.125 inches of the mine dust layer will be entrained in a coal dust explosion. Using a handheld pan and brush, it is difficult to correctly and repeatably sample a layer of this exact thickness.

The hand-held, pneumatic dust sampling device (DSD) is designed to provide mine operators, rock dusting crews, mine examiners and inspectors with a much improved ability to collect relevant, repeatable, and objective mine dust samples from a mine floor, roof, or ribs, and to avoid the uncertainty inherent in the present rock dust quality assessment process. The DSD mimics the dust entrainment process that happens in a coal dust explosion by blowing a puff of air over a surface laden with coal and rock dust, entrains a dust sample in the puff of air, and captures a mine dust sample for subsequent analysis of total inert content (TIC). When used in conjunction with the Coal Dust Explosibility Meter (CDEM), the device may be used to provide near instantaneous results on the quality of rock dusting at the tested location.

Referring now to FIG. 1, a DSD 2 comprises an air routing system 4, a charging or air containment vessel 6, and a sample chamber 8. Turning first to the air routing system 4, compressed air fitting 10 is the main connection for the air routing system to hook up to a source of compressed air for use in pneumatic operations. In the present embodiment, the DSD 2 is configured to run off of any compressed air line with a minimum pressure of fifty (50) psig, although in other embodiments the minimum pressure may be higher or lower. The compressed air source (not shown) may be a separate air reservoir (e.g. a compressed air line, a 5-gallon portable air tank, or a smaller air tank with an external regulator and a high internal charging pressure). The compressed air fitting 10 may use an adaptor or be changed out for a fitting of a different type if necessary to connect the air routing system 4 to the compressed air source.

The regulator 12 reduces the line pressure to a desired pressure—in the present embodiment, to approximately fifty (50) psig. The desired pressure may be determined based on the operating pressure of the pneumatic switch 20 (also referred to herein as a pneumatic trigger or a pneumatic switch trigger), which, in the present embodiment, is forty-five (45) psig. In some embodiments, for example, the desired pressure may be anywhere from twenty-five (25) to seventy-five (75) psig. Maintaining the line pressure above the operating pressure of the pneumatic switch 20 serves to prevent malfunction or non-function of the pneumatic switch 20 due to low pressure.

Compressed air provided to the air routing system via the compressed air fitting 10 flows through two separate lines after passing through the regulator 12. Air flowing through one line may pass through a pressure gauge 16 before reaching the button valve 14. The pressure gauge 16 is a one hundred and fifty (150) psig pressure gauge in the present embodiment, although other pressure gauges may be used in other embodiments. The particular pressure gauge used may be selected, for example, based on the pressure of the compressed air source, as well as the operating pressure of the DSD 2. The button valve 14 is biased toward or otherwise defaults to the closed position. When the button valve 14 is opened by a user of the DSD 2 (e.g. by depressing a button on the button valve 14), the compressed air flows through the button valve 14 and to the pneumatic switch 20, where it reaches the actuation port of the pneumatic switch 20 and switches the pneumatic switch 20 from a discharge/idle state to a charge state. In the charge state, the pneumatic switch 20 routes the compressed air through the pressure gauge 22 and into the charging vessel 6, which stores the compressed air until it is released to generate the puffs of air necessary for dust sample collection.

When the button valve 14 is released and thus allowed to return to its default (closed) state, the air between the button valve 14 and the pneumatic trigger 20 is released to the atmosphere, and the pneumatic switch 20, with atmospheric pressure only at the switch port 20a, switches from the charge state to the discharge/idle state.

Compressed air passing through the regulator 12 and flowing into the second line passes through the adjustable regulator 18. An air line exiting the adjustable regulator 18 connects to the switch port 20c of the pneumatic trigger 20, which is closed when the pneumatic trigger 20 is in the discharge/idle state and open when the pneumatic trigger 20 is in the charging state. Thus, the pressure in the air line between the adjustable regulator 18 and the pneumatic trigger 20 (e.g. the pressure to which the adjustable regulator 18 is set) is the pressure to which the charging vessel 6 will equalize as the button valve 14 is held in the open position for charging. In the present embodiment, the adjustable regulator 18 is set to between fifteen (15) and twenty-five (25) psig, although in other embodiments it may be set to higher or lower pressures. For example, in some embodiments the adjustable regulator 18 may be set to between ten (10) and thirty (30) psig. Because the pressure to which the adjustable regulator 18 is set determines the pressurization of the charge of air within the charging vessel 6, the adjustable regulator 18 effectively controls the speed at which air will be discharged from the charging vessel 6 and through the nozzles 24, which in turn affects the amount of dust that will be collected and the depth of the dust scour profile on the dust sampling surface following discharge of the charging vessel 6.

The pressure gauge 22 allows the user to ensure the charging vessel 6 reaches the desired pressure before conducting the dust sample test. In the current embodiment, the pressure gauge 22 is a thirty (30) psig gauge, although in other embodiments the pressure gauge 22 may be rated for higher or lower pressure. When the charging vessel 6 reaches the correct (i.e. desired or predetermined) pressure, the operator of the DSD 2 can release the button valve 14 and allow the pneumatic trigger 20 to switch to the discharge/idle state. When the switch occurs, the switch ports 20a and 20c of the pneumatic switch 20 close, and the switch ports 20b and 20d of the pneumatic switch 20 open. This allows the air in the charging vessel 6 to discharge through blowoff nozzles 24 into the sample chamber 8. When the charging vessel 6 discharges to ambient pressure, the sample collection is complete. Although not shown, a CDEM may be attached to the DSD 2 and configured to test a dust sample collected in the sample collection bag 28 as soon as the dust sample has been collected.

Figure 2:
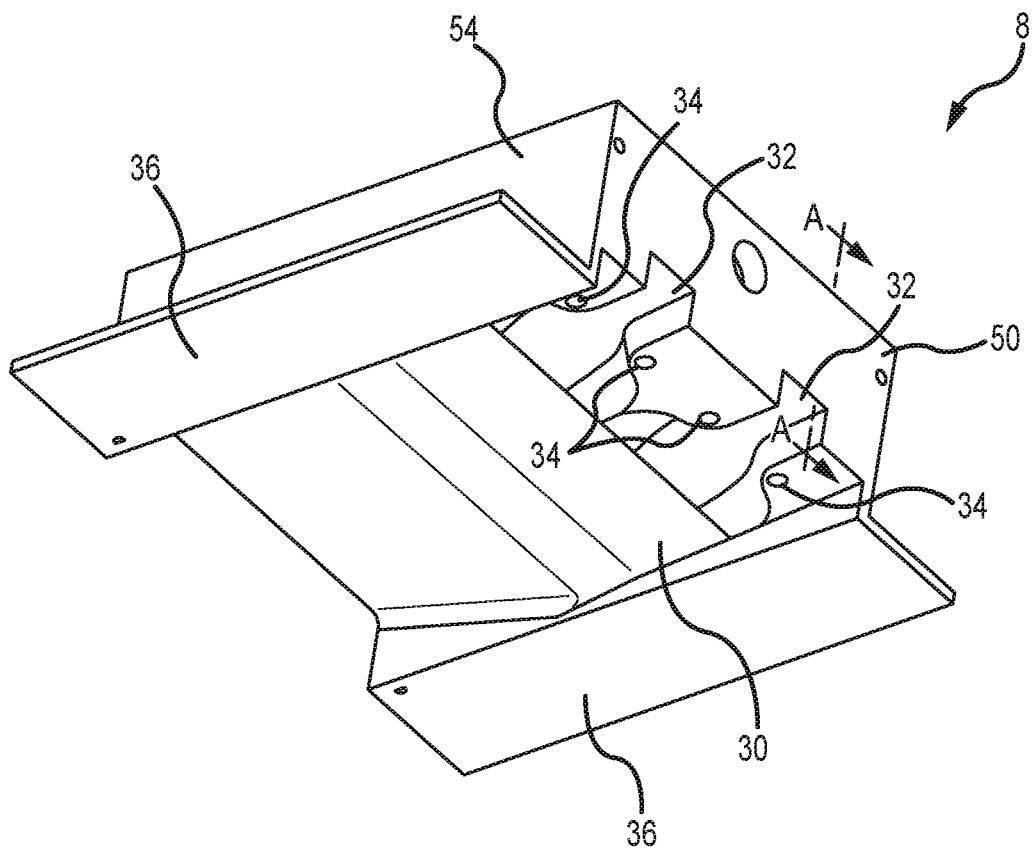
FIG. 2 depicts a sampling chamber of a pneumatic mine dust sampling instrument according to another embodiment of the present invention.

Turning now to FIG. 2, the various components of the DSD 2 may be mounted to and/or comprised within a housing 30, which may be made of aluminum or, in some embodiments, of other suitable material. The housing 30 is generally rectangular in cross section, with a front surface 50, a rear surface 52, and sidewalls 54. The housing 30 has fixed mounting brackets 32 to which the blowoff nozzles 24 may be mounted to ensure that they are located at the desired height and angle for sample collection. In the present embodiment, for example, the mounting brackets 32 are configured to fix the nozzles 24 parallel to the sidewalls 54 at a vertical angle of five (5) degrees below horizontal, with the bottom of the exhaust port of each nozzle 24 positioned even with the testing or sampling surface (e.g. 0.0 inches offset from the plane of the testing surface). The exhaust ports of the nozzles 24 are relatively flat, and serve to provide an even release of the compressed air from the charging vessel 6 to and over the sampling surface, while also focusing the air to create dust movement from the sampling surface to the sample collection bag 28. At a point even with and generally parallel to the exhaust ports of the nozzles 24, the bottom surface of housing 30 transitions from the nozzle mounting brackets 32 to the sample collection area 26, along the length of which the bottom or underside of the housing 30 has a steady incline that serves to reduce unwanted eddies in the air flow and enhance dust entrainment during discharge of the compressed air in the charging vessel 6.

The housing 30 has winged resting plates 36 extending from the bottom of the left and right sidewalls 54 of the housing 30 to assist with stabilization and placement of the DSD 2. In the present embodiment, the resting plates are roughly one (1) inch wide per side, and run the length of the housing 30. The dimensions of the housing 30 may be selected based on the intended use of the DSD 2 and the desired results of that use. In the present embodiment, the housing 30 has a length of from two (2) inches to five (5) inches, preferably from three (3) inches to four (4) inches, and more preferably of three and three-quarters (3.75) inches. Also in the present embodiment, the housing 30 has a width (not including the resting plates 36) of from one (1) inch to three (3) inches, preferably from one (1) inch to two (2) inches, more preferably of one and three-quarters (1.75) inches.

Figure 3:
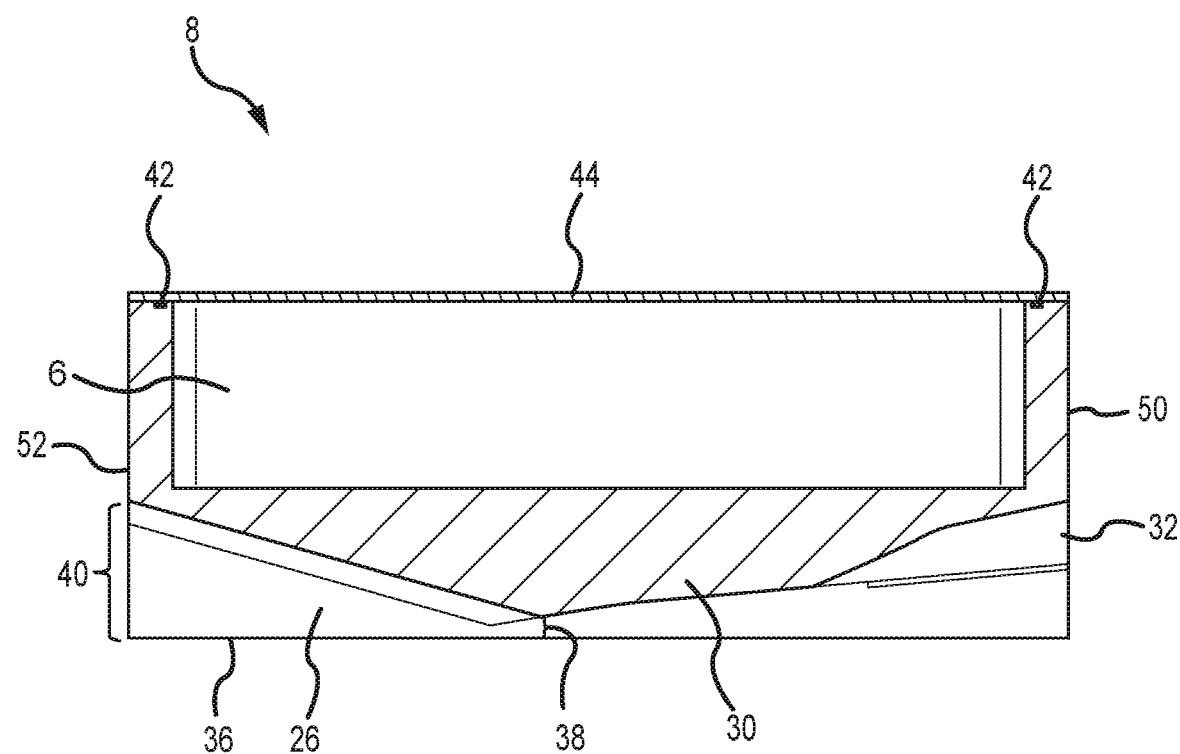
FIG. 3 depicts a cross-sectional view of the sampling chamber of FIG. 2, taken at line A-A of FIG. 2.

FIG. 3 depicts a cross section of the housing 30 taken along the length of the housing 30 and through the mid-plane of a nozzle mounting bracket 32. In this view, the inclined underside of the housing 30 in the sample collection area 26, which begins at the sample collection area inlet 38 and ends at the sample collection area outlet 40, is clearly visible. The sample collection area 26 has a simple vertical wedge design, with the narrowest or shortest portion at the nozzle exhausts (which is also the sample collection area inlet 38) and the widest or tallest portion where the sample collection bag 28 is secured (e.g. the sample collection area outlet 40). The shape of the sample collection area 26 is designed to reduce air recirculation over the sample area surface and help direct a dust sample into the sample collection bag 28. Also visible in FIG. 3 is the charging or air containment vessel 6, which in the present embodiment is formed in the upper portion of the housing 30. A gasket 42 provides an airtight seal between the upper lid 44 and the body 48 of the housing 30 to allow the charging vessel 6 to hold compressed air.

Figure 4:
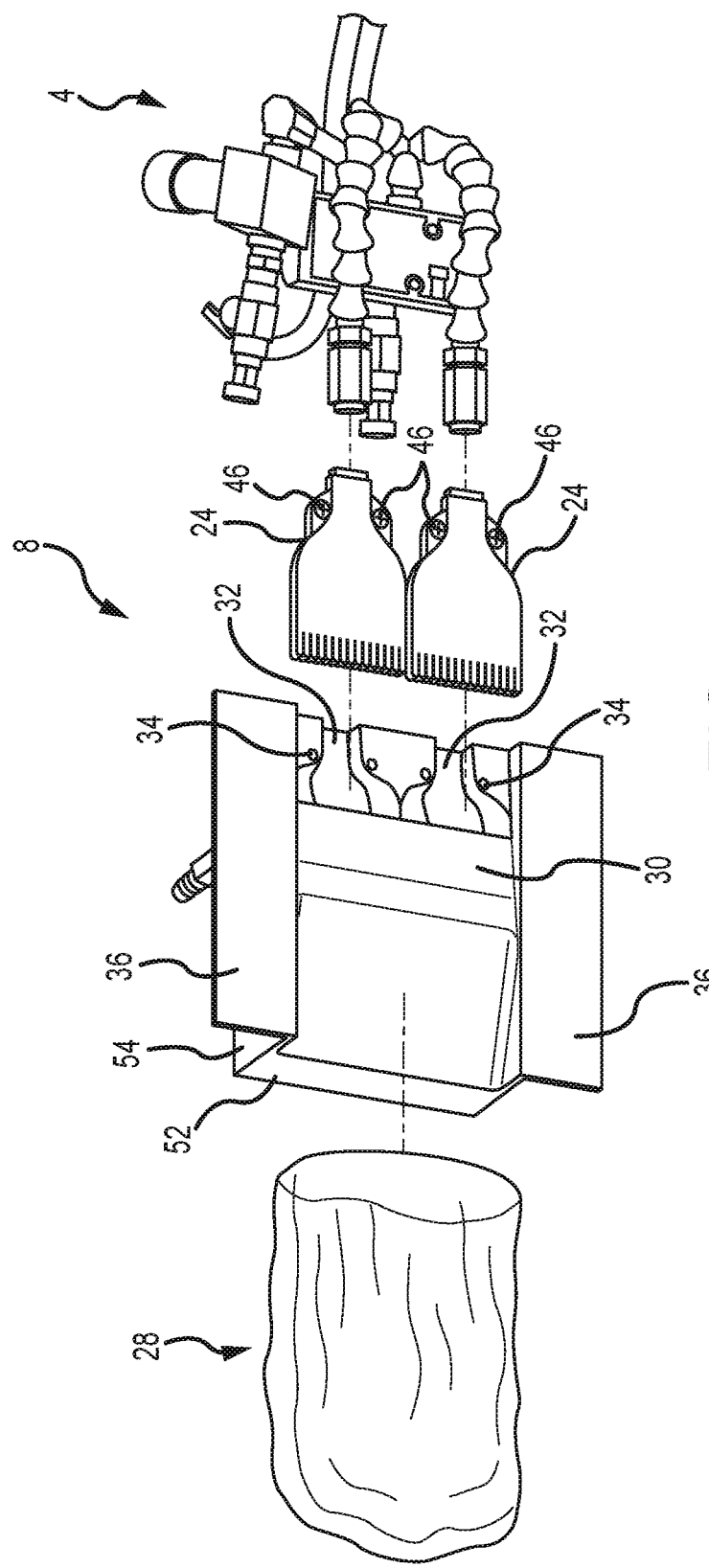
FIG. 4 depicts an exploded view of a pneumatic mine dust sampling instrument according to an embodiment of the present invention.

FIG. 4 provides a partially exploded view of the DSD 2, showing the air routing system 4, the nozzles 24, the housing 30 with sample collection area 26, and the sample collection bag 28. Also visible in the housing 30 are the mounting screw holes 34 for receiving mounting screws 46 that secure the nozzles 24 to the nozzle mounting brackets 32 of the housing 30.

The sample collection bag 28 may be secured to the outlet 40 of the sample collection area 26 using any suitable mechanism or means, including, but not limited to, with an elastic band, a drawstring, one or more ties, adhesive, and/or one or more mechanical fasteners. Preferably, the means used to connect the sample collection bag 28 to the sample collection area 26 provide a connection that is both sufficiently secure to not give way during the discharge of air from the charging vessel 6 and substantially airtight to minimize the escape of air and entrained dust from the sample collection area during the collection process. In some embodiments, the mechanism or means used to attach the sample collection bag 28 to the housing 30 may also be used to seal the sample collection bag 28 after a dust sample has been collected, e.g. to prevent the collected dust sample from escaping the sample collection bag 28.

In some embodiments, the housing 30 may be provided with a lip or flange around the edge of the sample collection area outlet 40 to facilitate attachment of the sample collection bag 28 to the sample collection area 26. In other embodiments, the sample collection bag 28 may be attached to the sample collection area outlet 40 using a collection bag attachment, which may be clipped or otherwise secured to the housing 30. A collection bag attachment may be used to create a solid seal between the sample collection bag 28 and the housing 30, so as to prevent air or dust sample leakage and loss. The collection bag attachment may also be used to allow easy removal of the sample collection bag 28 once the test is complete.

Figure 5:
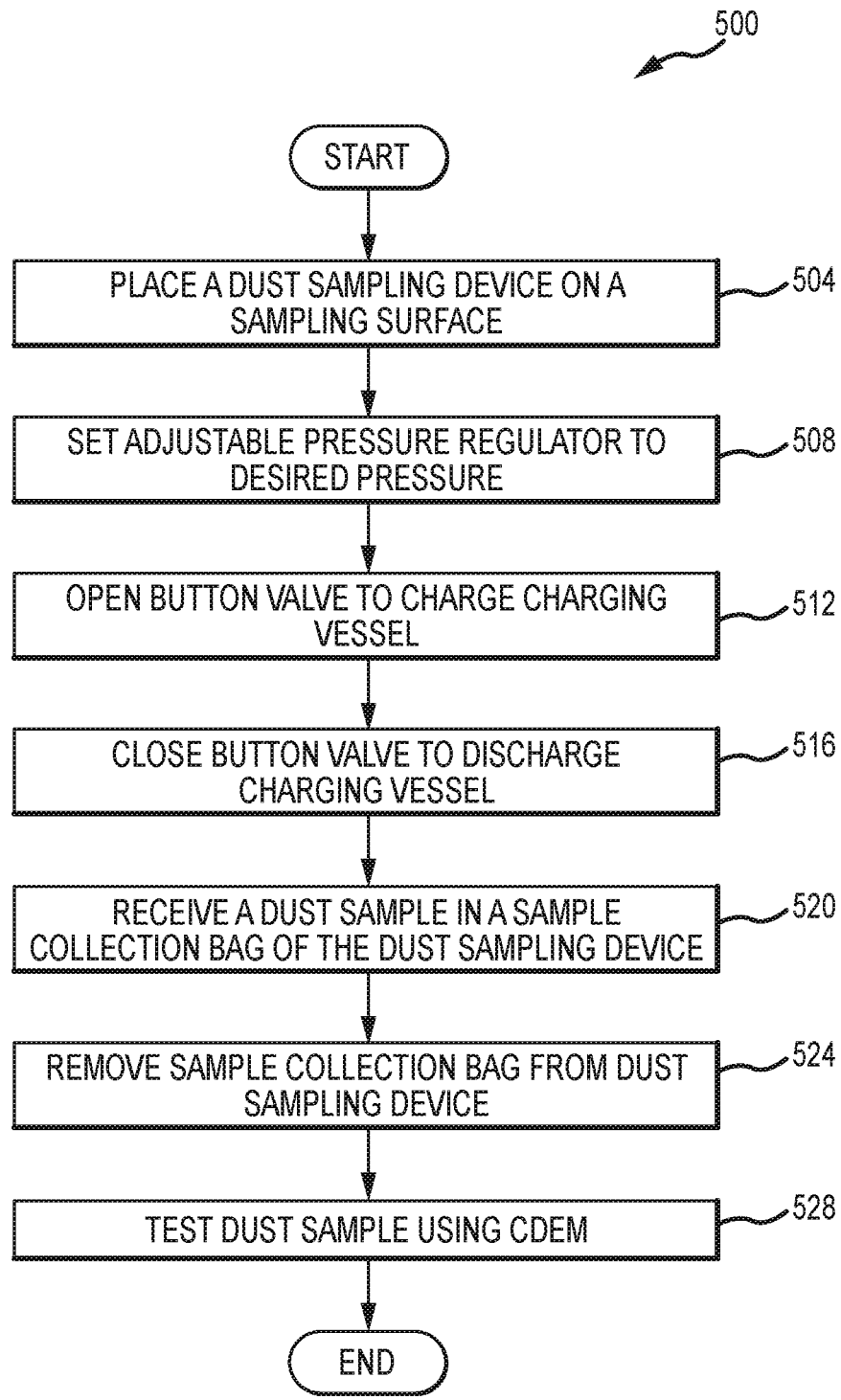
FIG. 5 is a flowchart showing a method of sampling dust according to one embodiment of the present invention.

With reference now to FIG. 5, a method 500 is provided for obtaining a dust sample. The method 500 comprises placing a dust sampling device on a sampling surface (step 504). The sampling surface may be the floor of a mine, a wall of a mine, a roof of a mine, a supporting column or beam, a wire mesh, a belt structure, one or more cables, one or more water lines, or any other surface from which dust may be sampled. Although described herein with respect to mines, a DSD 2 may be used in fields other than the mining field. For example, embodiments of the present invention may be used in any field that requires monitoring or controlling the level of dust or other particulates in a workplace or other environment (e.g. industrial clean rooms), as well as for hazardous material detection (e.g. detecting the amount of asbestos or lead in a dust sample). The dust sampling device may be, for example, a device such as the DSD 2.

The method 500 also comprises setting an adjustable pressure regulator to a desired pressure (step 508). In some embodiments, the adjustable pressure regulator may be set to any desired pressure between ten (10) psig and thirty (30) psig. In other embodiments, the adjustable pressure regulator may be set to any desired pressure between fifteen (15) and twenty-five (25) psig. Other pressure ranges may be utilized in other embodiments. The adjustable pressure regulator may, in some embodiments, have manual controls, while in other embodiments the adjustable pressure regulator may have electronic controls.

The method 500 further comprises opening a button valve to charge a charging vessel of the dust sampling device (step 512). The charging vessel may also be referred to as an air containment vessel. The button valve may, in some embodiments, allow compressed air at a pressure higher than the pressure to which the adjustable pressure regulator is set to flow around the adjustable pressure regulator and into a pneumatic switch. Upon arrival of the pressurized air from the button valve at the pneumatic switch, the pneumatic switch may switch from a discharge/idle state to a charge state. In the charge state, the pneumatic switch may allow the pressurized air from the button valve to flow through the pneumatic switch and into the charging vessel. The button valve may be kept in the open position until the charging vessel is charged to the pressure to which the adjustable regulator is set.

Also included in the method 500 is closing the button valve of the dust sampling device (step 516). Closing the button valve of the dust sampling device may stop the flow of compressed air around the adjustable pressure regulator, and allow any remaining compressed air in the line between the button valve and the pneumatic switch to be released to the atmosphere. The absence of pressure at the pneumatic switch in the line from the button valve may cause the pneumatic switch to switch from the charge state to the discharge/idle state, in which compressed air may flow from the charging vessel through the pneumatic switch and into the nozzle or nozzles of the dust sampling device. The nozzles may then direct the air onto and over the dust sampling surface, entraining dust from the dust sampling surface in the air as it flows out of the nozzle or nozzles and through a collection area of the dust sampling device. In some embodiments, the nozzle or nozzles of the dust sampling device may be configured to direct air onto the sampling surface at an angle between zero (0) and ten (10) degrees below horizontal. In further embodiments, for example, the nozzle or nozzles of the dust sampling device may be configured to direct air onto the sampling surface at an angle of five (5) degrees below horizontal.

The method 500 further includes receiving a dust sample in a sample collection bag of the dust sampling device (step 520). The sample collection bag may be affixed or attached to an outlet of the collection area of the dust sampling device, such that dust entrained in the air that flows out of the nozzle or nozzles of the dust sampling device is carried into the sample collection bag.

Once the dust sample has been received in the sample collection bag of the dust sampling device, the sample collection bag may be removed from the dust sampling device (step 524). In some embodiments, the sample collection bag may comprise a closure mechanism or means that allow the sample collection bag to be sealed after removal from the dust sampling device. Such closure mechanism or means may comprise, for example, an elastic band, a drawstring, one or more ties, a zipper, and/or one or more snaps.

The collected dust sample may be tested for inertness using a CDEM (step 528). The CDEM may be used, for example, to determine whether the coal dust meets federal standards for dust quality. For example, the CDEM may be used to determine whether the mine dust comprises sufficient inert material and will not propagate a coal dust explosion.

Figure 6:
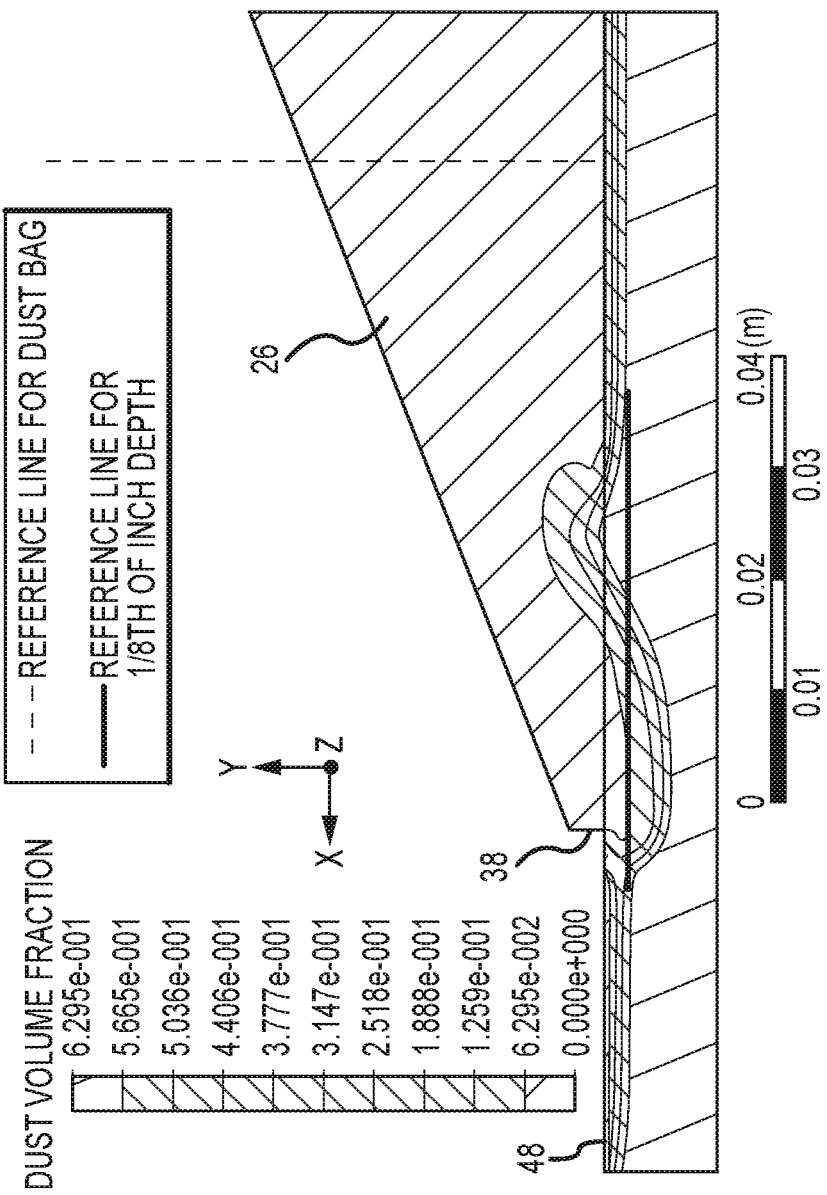
FIG. 6 is a graph showing results of a computational fluid dynamics analysis.
Figure 7:
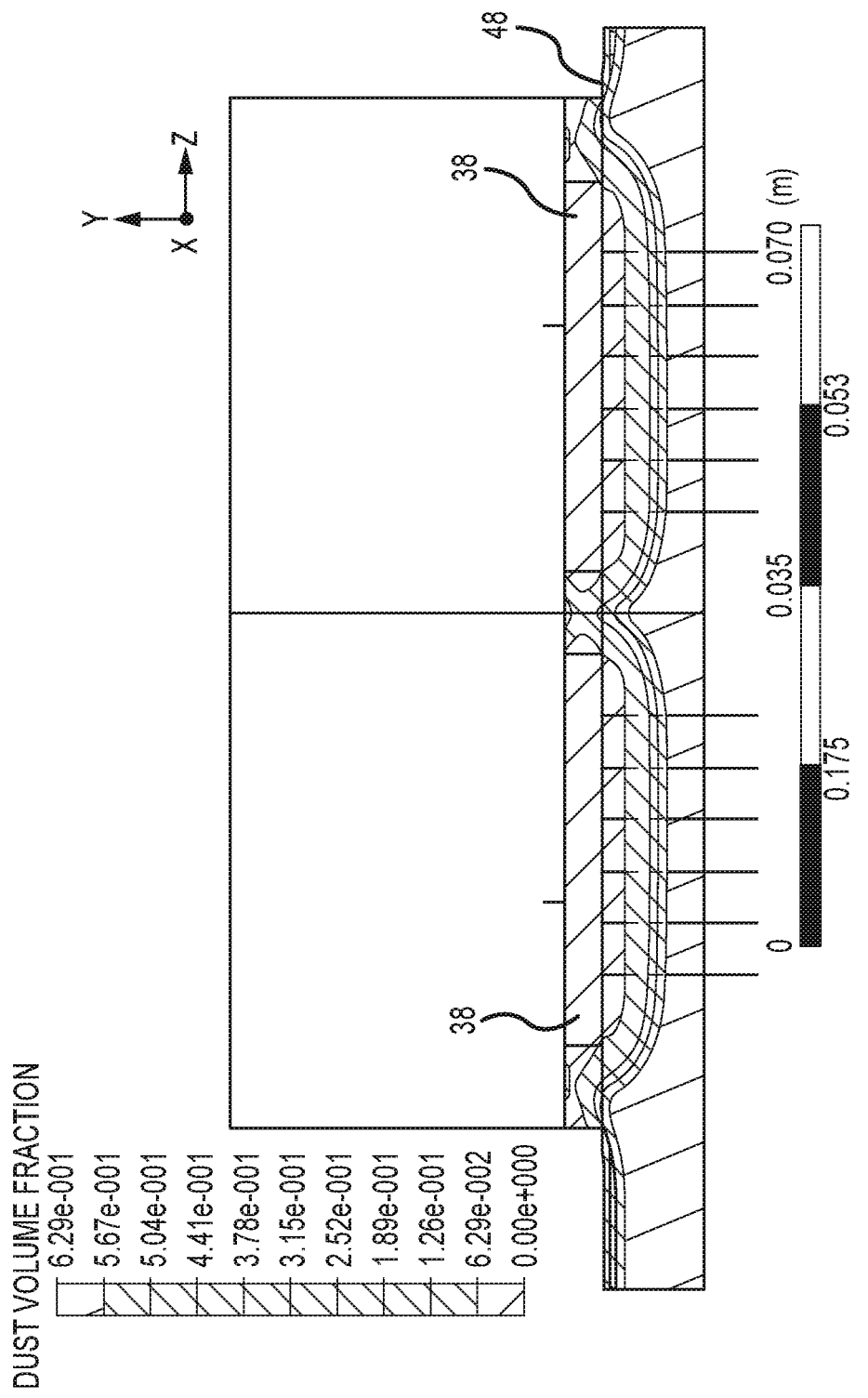
FIG. 7 is another graph showing results of a computational fluid dynamics analysis.

Provided in FIGS. 6 and 7 are computational fluid dynamics (CFD) images of the scour profile created within the sample collection area 26 of the DSD 2. FIG. 6 shows a CFD image of the scour profile created by the DSD as seen from the side of the sample collection area 26 (which has been placed on top of a dust bed 48), and FIG. 6 shows a CFD image of the scour profile created by the DSD as seen looking from the sample collection area outlet 40 toward the exhaust ports of the nozzles 24. The CFD models account for two material phases, air and rock dust particles, both of which are treated as fluids. The density and viscosity used for air are 1.23 kg/m$^3$ and 1.79E-05 kg/ms, respectively; for rock dust, 2,140 kg/m$^3$ and 1.003E-03 kg/ms, respectively. The fluid dynamics model for the area within the sample collection area 26 assumes a multi-phase flow with air as the primary phase and rock dust as the secondary phase. An Eulerian treatment was used, modelling both interacting phases separately. To solve the transient flow of air and dust particles, a viscous model with standard κ-epsilon parameters, standard wall treatment and dispersed turbulent multiphase flow was used. (See B. E. Launder et al., *Lectures in Mathematical Models of Turbulence*. Academic Press, London, England. 1972; D. Cokljat et al., *Multiphase k-epsilon Models for Unstructured Meshes*, ASME, Fluids Engineering Division, Summer 2000 Meeting, Boston, Mass. 2000.) In the model, rock dust is considered as a fluid with an assumed granular diameter of 7E-05 m.

The dust volume fraction is used as a reference to measure the depth of the scour. FIG. 6 shows the dust volume fraction at time=40 ms after the start of the air flow through the nozzles, along this reference plane. A reference line indicates the desired scour depth of ⅛th of an inch (3.2 mm). The dotted line (which is located at 6 cm to the right of the modeled nozzle exhaust port) represents the reference plane for the measurement of the dust collected.

To measure the scour profile predicted in the model, reference lines were created along the Y-axis at 0.2 cm from the nozzle at every 0.5 cm along the Z-direction, as shown in FIG. 7. Models show the depth of the scour profile ranging from 3 mm to 4 mm, which meets with the sampling depth of approximately ⅛ inch (3.2 mm) required by the MSHA (2013) dust sampling guidelines.

To validate the results, the CFD modeling results were compared with experimental testing. The following table illustrates that increasing the line pressure (e.g. changing the setting of the adjustable regulator) from 15 to 20 psig leads to a slightly deeper scour. Experimental data indicate an increase of 6% in scour depth while models differed by 5%.

|  | Scour Depth (mm) | | |
| --- | --- | --- | --- |
|  |  | Testing (n = 20) | |
| Pressure (psi) | CFD Model | Mean | St. Dev. |
| 15 | 3.2 | 3.1 | 0.4 |
| 20 | 3.3 | 3.3 | 0.8 |
| Difference in Scour Depth | 5% | 6% | |

The standard deviation and mean depth values presented above are based on the results obtained from twenty (20) tests performed at each pressure. Overall, the model shows excellent agreement with DSD prototype testing.

Testing was conducted with both a prototype dust sampling device and traditional pan and brush methods on two vertical rib locations and one inverted roof location. For all of these tests, rock dust was pitched onto the clean, dry wall-rock to create a sample surface for both methods. Through the vertical rib testing, it was discovered that placement of the dust sampling device did not disturb the wall sample or cause initial liberation of dust from the surface as researchers believed could occur. When the device sampling was initiated, small amounts of dust were dislodged and collected in the sample bags. The same conditions occurred during the inverted roof tests. The collected mass of these samples was low compared to the standard floor samples, but proved that the dust sampling device could be used to test a rib or roof in multiple locations to collect a usable sample.

Testing with the prototype dust sampling device was also conducted on wetted dust, including clumps of dust resulting from the applied moisture. Results showed the dust sampling device is capable of collecting the dry samples of dust that lay between the clumped and wet sections. This capability demonstrates one of the key benefits of the pneumatic sampling as compared to the pan-and-brush (PAB) method: the ability to replicate dust entrainment conditions during a mine explosion. Only dust dry enough to be entrained during an explosion would be sampled with the dust sampling device, leaving behind dust that is too wet to be entrained (whether by the dust sampling device or by an actual explosion). Using the PAB method, researchers could not collect a viable sample on the wet dust surface. The pan made poor contact with the heavy, rigid wet dust clumps that resulted from wetting, which allowed loose coal dust to be swept underneath the collection tray. The PAB method, then, would provide inaccurate results on a wetted surface, because a significant portion of the coal dust might be lost in the sampling process. Conclusions about the improved sampling effectiveness of the DSD over the PAB method on wet dust surfaces were similar to the tests conducted on the vertical and inverted surfaces, where the established one-eighth to one-fourth inch sampling depth may not be representative of the dust that would be entrained by an explosion pressure wave.

The present invention has significant benefits across a broad spectrum of endeavors. It is the Applicant's intent that this specification and the claims appended hereto be accorded a breadth in keeping with the scope and spirit of the present invention being disclosed despite what might appear to be limiting language imposed by the requirements of referring to the specific examples disclosed.

The phrases "at least one", "one or more", and "and/or", as used herein, are open-ended expressions that are both conjunctive and disjunctive in operation. For example, each of the expressions "at least one of A, B, and C", "at least one of A, B, or C", "one or more of A, B, and C", "one or more of A, B, or C," and "A, B, and/or C" means A alone, B alone, C alone, A and B together, A and C together, B and C together, or A, B, and C together.

Unless otherwise indicated, all numbers expressing quantities, dimensions, conditions, and so forth used in the specification, drawings, and claims are to be understood as being modified in all instances by the term "about."

The term "a" or "an" entity, as used herein, refers to one or more of that entity. As such, the terms "a" (or "an"), "one or more" and "at least one" can be used interchangeably herein.

The use of "including," "comprising," or "having," and variations thereof, is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts, and the equivalents thereof, shall include all those described in the summary of the present invention, brief description of the drawings, detailed description, abstract, and claims themselves.

The foregoing description of the present invention has been presented for illustration and description purposes. However, the description is not intended to limit the present invention to only the forms disclosed herein. In the foregoing Detailed Description for example, various features of the present invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the present invention.

Consequently, variations and modifications commensurate with the above teachings and skill and knowledge of the relevant art are within the scope of the present invention. The embodiments described herein above are further intended to explain best modes of practicing the present invention and to enable others skilled in the art to utilize the invention in such a manner, or include other embodiments with various modifications as required by the particular application(s) or use(s) of the present invention. Thus, it is intended that the claims be construed to include alternative embodiments to the extent permitted by the prior art.

What is claimed is:

1. A dust sample collecting device, comprising:
a housing with a front surface, a back surface, a plurality of sidewalls, and an underside, the underside having a first portion defining at least one nozzle mounting bracket and a second portion defining a collection area having an inlet, an outlet, and a wedge-shaped cross-section;
at least one nozzle having an intake port and an exhaust port, the at least one nozzle attached to the at least one nozzle mounting bracket with the exhaust port positioned at the inlet to the collection area and configured to discharge air into the collection area at a downward angle between zero and ten degrees below horizontal;
a sample collection bag having a single opening, the single opening removably attached around the outlet of the collection area to receive dust entrained by discharged air in the collection area; and
wherein the housing further comprises a compressed air containment vessel in selective fluid communication with the intake port of the nozzle and configured to store compressed air at a pressure between ten and thirty psig.

2. The dust sample collecting device of claim 1, wherein the housing further comprises a plurality of resting plates, each resting plate extending from a bottom of one of the plurality of sidewalls.

3. The dust sample collecting device of claim 1, wherein the at least one nozzle is configured to eject air from the exhaust port at a downward angle of five degrees below horizontal.

4. The dust sample collecting device of claim 1, wherein the outlet of the collection area is aligned with the back surface of the housing.

5. The dust sample collecting device of claim 1, wherein the second portion of the underside comprises a planar surface.

6. The dust sample collecting device of claim 5, wherein the inlet of the collection area comprises a first height, the outlet of the collection area comprises a second height greater than the first height, a forward end of the planar surface defines an upper boundary of the inlet, and a rearward end of the planar surface defines an upper boundary of the outlet.

7. The dust sample collecting device of claim 1, wherein the compressed air containment vessel stores compressed air at a pressure between 15 and 25 psig.

8. The dust sample collecting device of claim 1, wherein the collection area comprises: an inlet lower boundary and an inlet upper boundary; and an outlet lower boundary and an outlet upper boundary; wherein the inlet lower boundary and the outlet lower boundary define a first plane, and the inlet upper boundary and the outlet upper boundary define a second plane that intersects the first plane at a point between a third plane defined by the nozzle intake port and a fourth plane defined by the nozzle exhaust port.

9. A dust sample collecting device, comprising:
a housing with a front surface, a back surface, a plurality of sidewalls, and an underside, the underside having a first portion defining a nozzle mounting bracket and a second portion with a planar surface, the second portion defining a collection area having an inlet, an outlet, and a wedge-shaped cross-section, wherein the inlet of the collection area comprises a first height and the outlet of the collection area comprises a second height greater than the first height, and wherein a forward end of the planar surface of the housing underside defines an upper boundary of the inlet and a rearward end of the planar surface of the housing underside defines an upper boundary of the outlet;
a nozzle having an intake port and an exhaust port, the nozzle attached to the nozzle mounting bracket with the exhaust port positioned at the inlet to the collection area and configured to discharge air into the collection area at a downward angle between zero and ten degrees below horizontal;
a sample collection bag having an opening removably attached to the outlet of the collection area to receive dust entrained by discharged air in the collection area; and
a compressed air containment vessel in selective fluid communication with the intake port of the nozzle and configured to store compressed air at a pressure of between ten and thirty psig.

10. The device of claim 9, wherein the housing further comprises a plurality of resting plates, each resting plate extending from one of the plurality of sidewalls.

11. The device of claim 9, wherein the nozzle is configured to eject air from the exhaust port at a downward angle of approximately five degrees below horizontal.

12. The device of claim 9, wherein the nozzle is configured to eject air from the exhaust port at a downward angle of five degrees below horizontal.

13. The device of claim 9, wherein the compressed air containment vessel is configured to store compressed air at a pressure of between 15 and 25 psig.

14. The device of claim 9, wherein the inlet comprises a lower boundary and the outlet comprises a lower boundary, wherein the lower boundary of the inlet and the lower boundary of the outlet define a first plane, and wherein the upper boundary of the inlet and the upper boundary of the outlet define a second plane that intersects the first plane at a point between a third plane defined by the nozzle intake port and a fourth plane defined by the nozzle exhaust port.

15. A dust sample collecting device, comprising: a housing including a front surface, a back surface, a plurality of sidewalls, and an underside, the underside having a first portion defining a mounting bracket for at least one nozzle and a second portion defining a collection area with a wedge-shaped cross-section and including an inlet and an outlet, the inlet having an inlet lower boundary and an inlet upper boundary, the outlet having an outlet lower boundary and an outlet upper boundary; at least one nozzle having an intake port and an exhaust port, the at least one nozzle attached to the mounting bracket with the exhaust port configured to discharge air into the collection area at a downward angle between zero and ten degrees below horizontal, wherein the inlet lower boundary and the outlet lower boundary define a first plane and the inlet upper boundary and the outlet upper boundary define a second plane that intersects the first plane at a point between a third plane defined by the intake port of the at least one nozzle and a fourth plane defined by the exhaust port of the at least one nozzle; a sample collection bag having an opening removably attached to the outlet of the collection area to receive dust entrained by discharged air in the collection area; and a compressed air containment vessel in selective fluid communication with the intake port of the at least one nozzle and configured to store compressed air at a pressure between ten and thirty psig.

16. The sample collecting device of claim 15, wherein the housing further comprises a plurality of resting plates, each resting plate extending from one of the plurality of sidewalls.

17. The sample collecting device of claim 15, wherein the at least one nozzle is configured to discharge air from the exhaust port at a downward angle of five degrees below horizontal.

18. The sample collecting device of claim 15, wherein the second portion of the underside comprises a planar surface.

19. The sample collecting device of claim 15, wherein the compressed air containment vessel is configured to store compressed air at a pressure of between 15 and 25 psig.

* * * * *